United States Patent [19]

Jeong et al.

[11] Patent Number: 6,149,944
[45] Date of Patent: Nov. 21, 2000

[54] PREPARATION METHOD FOR BIODEGRADABLE POLYMERIC MICROSPHERES USING SOLVENT EXTRACTION AND PREPARATION METHOD FOR MICROSPHERES FOR TREATING LOCAL INFLAMMATION USING THE SAME

[75] Inventors: Seo Young Jeong, Koyang; Ick Chan Kwon; Yong-Hee Kim, both of Seoul, all of Rep. of Korea

[73] Assignee: Korea Institute of Science and Technology, Seoul, Rep. of Korea

[21] Appl. No.: 09/155,629

[22] PCT Filed: Apr. 1, 1997

[86] PCT No.: PCT/KR97/00055

§ 371 Date: Aug. 2, 1999

§ 102(e) Date: Aug. 2, 1999

[87] PCT Pub. No.: WO97/36949

PCT Pub. Date: Oct. 9, 1997

[30] Foreign Application Priority Data

Apr. 1, 1996 [KR] Rep. of Korea .................. 96/9755

[51] Int. Cl.[7] ................ A61K 9/50; B01J 13/02; B65B 13/02; B29B 13/02; B32B 5/16

[52] U.S. Cl. .............. 424/501; 264/4.32; 264/4.33; 264/4.6; 428/402.1

[58] Field of Search .................. 424/501; 264/4.32, 264/4.33, 4.6; 428/402.1

[56] References Cited

U.S. PATENT DOCUMENTS 5,445,832  8/1995  Orsolini et al. .
5,478,564  12/1995  Wantier et al. .
5,753,234  5/1998  Lee et al. .............. 424/204.1

FOREIGN PATENT DOCUMENTS 0 595 030  5/1994  European Pat. Off. .

*Primary Examiner*—Carlos A. Azpuru
*Attorney, Agent, or Firm*—Darby & Darby

[57] ABSTRACT

A preparation method for biodegradable polymeric microspheres using a solvent extraction method for biodegradable polymeric microspheres for treating a local inflammation disease using the same which are capable of effectively curing ozena such as sinusitis and a middle ear infection. Since a non-solvent of polymer is added into an outer aqueous phase in advance, the solidification of the polymer is implemented in a short time which, in turn, improves encapsulation of the therapeutic agent used.

2 Claims, No Drawings

PREPARATION METHOD FOR BIODEGRADABLE POLYMERIC MICROSPHERES USING SOLVENT EXTRACTION AND PREPARATION METHOD FOR MICROSPHERES FOR TREATING LOCAL INFLAMMATION USING THE SAME

This application is a 371 continuation of PCT/KR97/00055 filed Apr. 1, 1997, which is a continuation of KR19669755 filed Apr. 1, 1996.

FIELD OF THE INVENTION

The present invention relates to an improved preparation method for a biodegradable polymeric microspheres using a solvent extraction method and a preparation method for biodegradable polymeric microspheres for treating local inflammation disease, in particular, for treating sinusitis and middle ear inflammation.

DESCRIPTION OF RELATED ART

Esters, especially a single or combined polymeric esters consisting of a single molecule of a lactic acid and a glycolic acid have received much attention in the development of a sustained medicine delivery system due to their high biocompatibility, biodegradability and applicability for the human body as recognized for its stable usage as suture. Generally, they have been employed in the form of microspheres, transplantates, and fibers. Various microspheres preparation methods using a biodegradable polymeric ester have been reported. Among these, a solvent evaporation method is widely used. This method is directed to dissolving a polymer in a proper solvent and then dissolving or dispersing a therapeutic agent, which in turn, is dispersed in an aqueous phase containing a surface active agent. Thereafter, it is heated to evaporate the solvent of the polymer to obtain microspheres.

Since this method is useful for encapsulation of only hydrophobic medicine due to its characteristic preparation process, recently there has been developed a W/O/W type emulsion method which is directed to separately fabricating an aqueous phase containing a water soluble medical agent, then dispersing the same into an organic phase, whereby it is possible to enhance the encapsulation efficiency of the agent. In addition, there is disclosed a solvent diffusion method which is directed to adding a water-soluble solvent such as acetone to an organic solvent being a solvent of a polymer, in order to easily diffuse the organic solvent into an outer aqueous phase. Recently, a solvent extraction method has been developed to solidify a polymer by extracting an organic solvent with a non-solvent which cannot dissolve the polymer but is well mixed with the solvent of the polymer.

SUMMARY OF THE INVENTION

Accordingly, it is an object of the present invention to provide an improved preparation method for biodegradable polymeric microspheres using a solvent extraction method and a preparation method for biodegradable polymeric microspheres for treating local inflammation using the same which overcome the aforementioned problems encountered in the conventional art.

It is another object of the present invention to provide an improved preparation method for biodegradable polymeric microspheres using a solvent extraction method and a preparation method for microspheres for treating local inflammation using the same which are capable of more effectively preventing a decrease of an encapsulation efficiency of an agent compared to the conventional solvent extraction method.

It is another object of the present invention to provide an improved preparation method for biodegradable polymeric microspheres using a solvent extraction method and preparation method for microspheres for treating local inflammation using the same which are basically directed to developing a continuously releasing therapeutic agent in order to cure a local inflammative disease.

It is another object of the present invention to provide an improved preparation method for biodegradable polymeric microspheres using a solvent extraction method and preparation method for microspheres for treating a local inflammation disease using the same which are capable of effectively curing ozena such as sinusitis and a middle ear inflammation.

The preparation method for biodegradable polymeric microspheres according to the present invention includes a step for first preparing a W/O type emulsion by mixing an inner aqueous phase and an organic phase comprising an organic solvent of polymer in which a biodegradable polymer is dissolved, and then well dispersing the resulting emulsion;

a step for preparing an outer aqueous phase wherein a non-solvent of the polymer is dissolved;

a step for adding the aforementioned W/O type emulsion into the outer aqueous phase to prepare a W/O/W type emulsion; and a step for removing an organic solvent of polymer.

The preparation method for biodegradable polymeric microspheres for treating local inflammation disease according to the present invention includes a step for preparing a W/O type emulsion by mixing an inner aqueous phase containing water-soluble betalactam antibiotic agent and/or an inhibitor of betalactamase and an organic phase comprising an organic solvent of polymer in which a biodegradable polymer is dissolved, and then well dispersing the resulting emulsion;

a step for preparing an outer aqueous phase wherein a non-solvent of the polymer is dissolved;

a step for adding the aforementioned W/O type emulsion into the outer aqueous phase to prepare a W/O/W type emulsion; and a step for removing an organic solvent of polymer.

Additional advantages, objects and features of the invention will become more apparent from the description which follows.

DETAILED DESCRIPTION OF THE INVENTION

Ozena such as sinusitis and a middle ear inflammation is generally caused by bacteria which invade from exterior environment and is not effectively cured because the lesions of the diseases are surrounded by bones. Therefore, it is difficult to treat the disease by a systemic therapeutic approach. So, in order to effectively cure the above-described disease, a medicine which has a continuous and long time therapeutic effect is required. In addition, when curing such disease, since the portion of the disease should be opened, it is impossible to adopt a transplantate. Therefore, in order to maintain an open state and to continuously release the medicine, encapsulation method of an antibiotic into a microspheres was conjectured.

In the present invention, in order to insert a water-soluble therapeutic agent into a biodegradable polymeric ester microspheres, in particular into a polylactic acid, a W/O/W type emulsion method is used, and a solvent extraction method is used in order to increase an encapsulation efficiency of the therapeutic agent used.

Namely, unlike the conventional method wherein a non-solvent is added after the fabrication of the W/O/W type emulsion, in order to remove the solvent of the polymer, an improvement of the present method in view of the prior art lies in that the non-solvent is mixed with the outer aqueous phase in advance to fabricating the W/O/W type emulsion. Thus, according to the present invention, the solidification of the polymer is implemented within a short time, so thus increasing the encapsulation efficiency of the agent.

In the present invention, the non-solvents of the polymer can be mentioned acetaldehyde, acetonitrile, acetone, acrolein, allyl alcohol, aniline, benzylalcohol, butylalcohol, carbon disulfide, cyclohexanol, dichlorobenzene, diethyleneglycol, diethylsulfone, dimethylacetamide, dimethylform amide, dimethylsufoxide, 1,4-dioxane, dipropylsulfone, ethylacetamide, ethylalcohol, ethylamide, ethyl acetate, ethylenediamine, ethyleneoxide, ethylformamide, formic acid, furfurylalcohol, heptylalcohol, hexandiol, hexylalcohol, iodobenzene, methanol, methylamine, methylbenzoate, methyleneglycolate, methylethylsulfone, methylformate, methylpropylsulfone, octylalcohol, 1,5-pentandiol, phenylhydrazine, propylalcohol, isopropylalcohol, propyleneglycol, pyridine, styreneoxidil, and etc. Among them, ethylacetate is preferably used, for thus fabricating a desired super microspheres. The concentration thereof is 0.5–10 wt. % with respect to the outer aqueous phase.

In the present invention, the concentration of polylacticacid is preferably 1–15 wt. %.

In the present invention, a surface active agent which is added into the organic solvent can be fatty acids, olefins, alkyl carbons, silicones, sulfate esters, fatty alcohol sulfates, sulfated fats and oils, sulfonic acid salts, aliphatic sulfonates, alkylaryl sulfonates, lignin sulfonates, phosphoric acid esters, polyoxyethylenes, polyglycerols, polyols, imidazolines, alkanol amines, hetamines, sultomethamines, phosphatides, and Span 20, Span 40, Span 60 and Span 80, etc. Among them, Span is preferably used, and the content thereof is 1–10%. In the present invention, as an organic solvent of polymer, methylene chloride is preferred, and the ratio between the inner aqueous phase and organic phase is 1:1–1:20.

In the present invention, as a surface active agent of the outer aqueous phase, 0.1–5 wt./part of polyvinyl alcohol is added to 100 wt. part of water, and the volume ratio of the outer aqueous phase to the organic phase is preferably 200:1.

The therapeutic agents which can be used in the present invention are betalactam antibiotics such as ampicillin, amoxicillin, and their salts and inhibitors of betalactamase such as sulbactam and clavulanic acid. It is possible to reduce the resistance of microorganisms to the antibiotics by effectively combining the above two kinds of agents.

In addition, in the present invention, when fabricating a W/O/W type emulsion, a stirrer, homogenizer, ultrasonic apparatus, etc. may be used.

Next, an example of the present invention will now be explained. However, the following example is not limited to the disclosed description.

Example I

As an inner aqueous phase, amoxicillin sodium was dissolved in distilled water as saturation concentration and as an organic phase, 10 wt. part of polylactic acid and 5 wt. part of Span 80 were dissolved in 100 wt. part of methylene chloride. Then, 2 wt./part of ethyl acetate is dissolved in 98 wt. part of an aqueous solution which is formed by dissolving 0.5 wt. part of polyvinyl alcohol in 100 wt. part of distilled water, for thus forming an outer aqueous phase. The inner aqueous phase and the organic phase were mixed in the volume ratio of 1:12.5 by using a vortex to give a W/O type emulsion, and then the resultant mixture was well dispersed by using a ultrasonic apparatus. Thereafter, the outer aqueous phase is uniformly agitated by using a homogenizer at 1000–8000rpm, and the aforementioned W/O type emulsion was slowly added into the outer aqueous phase in the volume ratio of 1:200 to obtain a W/O/W type emulsion. The multiple emulsion was agitated for about 30 minutes to remove the organic solvent of the polymer and filtered, and then was dried in a vacuum oven for one day, for thus fabricating biodegradable polymeric microspheres.

Example II

As an inner aqueous phase, sulbactam sodium was dissolved in distilled water as saturation concentration and as an organic phase, 10 wt. part of polylactic acid and 5 wt. part of Span 80 were dissolved in 100 wt. part of methylene chloride. Then, 2 wt./part of ethyl acetate is dissolved in 98 wt. part of an aqueous solution which is formed by dissolving 0.5 wt. part of polyvinyl alcohol in 100 wt. part of distilled water, for thus forming an outer aqueous phase. The inner aqueous phase and the organic phase were mixed in the volume ratio of 1:16.7 by using a vortex to give a W/O type emulsion, and then the resultant mixture was well dispersed by using a ultrasonic apparatus. Thereafter, the outer aqueous phase is uniformly agitated by using a homogenizer at 1000–8000 rpm, and the aforementioned W/O type emulsion was slowly added into the outer aqueous phase in the volume ratio of 1:200 to obtain a W/O/W type emulsion. The multiple emulsion was agitated for about 30 minutes to remove the organic solvent of the polymer and filtered, and then was dried in a vacuum oven for one day, for thus fabricating biodegradable polymeric microspheres.

Comparative Example

The conventional method (a solvent extraction method) wherein a W/O/W type emulsion is prepared in which a non-solvent is not provided and a non-solvent is added therto at a later stage and a method (an improved solvent extraction method) of the present invention wherein a non-solvent of a polymer exists in the outer aqueous phase from the beginning are compared with each other with respect to an agent encapsulation ratio (%) and an agent encapsulation efficiency (%) as follows:

Agent encapsulation ratio (%)=(the amount of agents in microspheres/the taken amount of microspheres)×100

Agent encapsulation efficiency (%)=(the amount of agents in microspheres/the initial addition amount of agents)×100

| Microspheres preparation method | Agent-encapsulation ratio (%) | Agent-encapsulation efficiency (%) |
|---|---|---|
| Conventional solvent extraction method | 12.33 | 41.1 |
| Example I | 17.93 | 59.4 |

Although the preferred embodiments of the present invention have been disclosed for illustrative purposes, those skilled in the art will appreciate that various modifications, additions and substitutions are possible, without departing from the scope and spirit of the invention as recited in the accompanying claims.

What is claimed is:

1. A preparation method for a biodegradable polymeric microspheres for treating local inflammation disease, comprising:

a step for preparing a W/O emulsion by mixing an inner aqueous phase containing water-soluble betalactam antibiotic agent and/or an inhibitor of betalactamase and an organic phase comprising an organic solvent of polymer in which a biodegradable polymer is dissolved, well dispersing the resulting emulsion;

a step for preparing an outer aqueous phase wherein a non-solvent of the polymer is dissolved in an aqueous solution of distilled water containing a surface active agent;

a step for adding the aforementioned W/O emulsion into the said outer aqueous phase to prepare a W/O/W emulsion; and a step for removing the organic solvent of the polymer.

2. The method of claim 1, wherein said betalactam antibiotic agent is ampicillin, amoxycilin, or salts thereof, and said inhibitor of a betalactamase is sulbactam, clavulanic acid or salts thereof.

* * * * *